United States Patent [19]

Bridges et al.

[11] Patent Number: 5,571,904
[45] Date of Patent: Nov. 5, 1996

[54] MALE FLOWER SPECIFIC GENE SEQUENCES

[75] Inventors: Ian G. Bridges, Slater, Iowa; Simon W. J. Bright, Marlow, England; Andrew J. Greenland, Maidenhead; Wolfgang W. Schuch, Crowthorne, both of Great Britain

[73] Assignee: Zeneca Limited, London, England

[21] Appl. No.: 266,313

[22] Filed: Jun. 27, 1994

Related U.S. Application Data

[63] Continuation of Ser. No. 141,553, Oct. 25, 1993, abandoned, which is a continuation of Ser. No. 929,494, Aug. 18, 1992, abandoned, which is a continuation of Ser. No. 931,310, Jul. 17, 1991, abandoned, which is a continuation of Ser. No. 470,604, Jan. 26, 1990, abandoned.

[30] Foreign Application Priority Data

Jan. 26, 1989 [GB] United Kingdom .................... 8901697

[51] Int. Cl.$^6$ .............................. C12N 15/11; A01H 1/00
[52] U.S. Cl. ......................... 536/24.1; 47/58; 47/DIG. 1
[58] Field of Search .................................. 536/23.6, 24.1; 435/320.1, 172.3; 935/35, 68, 64, 67

[56] References Cited

PUBLICATIONS

Journal of Cellular Biochemistry, Supplement 12C, UCLA Symposium on the Molecular Basis of Plant Development, 26 Mar.–2 Apr. 1988, Alan R. Liss, Inc., (New York, US) A. J. Greenland et al.: "Isolation and characterisation of developmentally expressed genes from maize tassels", p. 171, abstract L 208.

UCLA Symp. Mol. Cell. Biol. New Ser., vol. 92 (Mol. Basis Plant Dev.), 1989, Alan R. Liss, Inc., J. P. Mascarenhas: "Characterization of genes that are expressed in pollen", pp. 99–105 and Proceedings of an E. I. du Pont de Nemours–UCLA Symposium, Steamboat Springs, Colorado, 26 Mar.–2 Apr. 1988.

Journal of Cellular Biochemistry, Supplemental 12C, 1988, UCLA Symposium on the Molecular Basis of Plant Development, 26 Mar.–2 Apr. 1988, Alan R. Liss, Inc., (New York, US), C. S. Gasser et al.: "Analysis of flora specific genes", p. 137, abstract L 021.

Chemical Abstracts, vol. 106, 1987 (Columbus, Ohio, US), J. R. Stinson et al.: "Genes expressed in the male gametophyte of flowering plants and their isolation", see p. 175, abstract 150569p, and Plant Physiol. 1987, 83(2), 442–7.

D. A. Hamilton et al. "Characteriszation of a pollen–specific genomic clone from maize" Sex Plant Reproduction––Springer–Verlag 1989, 2:208–212.

D. D. Hanson et al. "Characterization of a Pollen–Specific cDNA Clone from Zea mays and Its Expression", The Plant Cell, 1:173–179, (1989) American Society of Plant Physiologists.

Stinson, J. P. et al. (1987) "Genes Expressed in The Male Gometophyte of Flowering Plants and Their Isolation" Plant Physiology, vol. 83 pp. 442–447.

*Primary Examiner*—Gary Benzion
*Attorney, Agent, or Firm*—Cushman Darby & Cushman, L.L.P.

[57] ABSTRACT

Three similar gene sequences are provided, the sequences being shown in the drawings, which are recovered from male flower parts of maize, specifically anther tissue. When one or more of these sequences are included in a gene construct, expression of an encoded protein is restricted to male parts of the plant. The sequences have utility in any application where expression in male flower parts is indicated, a specific application is in the control of expression of a disrupter protein which imparts male sterility when incorporated in a plant genome.

6 Claims, 18 Drawing Sheets

FIG. 4(A)

Nucleotide and deduced amino acid sequence for male flower specific cDNA clone, pMS10.

```
              10                  20                  30                  40
               |                   |                   |                   |
    GGC CTT GCC CGC TCG TTC CCC TCG CCT CCC CGG TCG CGC CGC TCC 50                  60                  70                  80                  90
               |                   |                   |                   |                   |
    CGC TGC CGC CGT GGC GAT TCC TGC CCG GCG GCG GCG CCG GGT TCA 100                 110                 120                 130
               |                   |                   |                   |
    GGT CCA CGG CGG CGG CGG CTG CGC GGG GCG GGA CCG ACT ATG GGA
                                                             Met Gly 140                 150                 160                 170                 180
               |                   |                   |                   |                   |
    CGG ACG ACA GCA AGA TCT CCC CCG ACG AGG AAT TCC TTC GAG GGC
    Arg Thr Thr Ala Arg Ser Pro Pro Thr Arg Asn Ser Phe Glu Gly 190                 200                 210                 220
                       |                   |                   |                   |
    TGC GAC TAC AAC CAC TGG CTC ATC ACC ATG GAC TTC CCG GAC CCC
    Cys Asp Tyr Asn His Trp Leu Ile Thr Met Asp Phe Pro Asp Pro 230                 240                 250                 260                 270
               |                   |                   |                   |                   |
    AAG CCG TCG CGC GAA GAG ATG ATC GAG ACA TAC CTC CAG ACT CTC
    Lys Pro Ser Arg Glu Glu Met Ile Glu Thr Tyr Leu Gln Thr Leu 280                 290                 300                 310
                       |                   |                   |                   |
    GCC AAG GTC GTC GGG AGT TAT GAG GAG GCC AAG AAG AGG ATG TAT
    Ala Lys Val Val Gly Ser Tyr Glu Glu Ala Lys Lys Arg Met Tyr 320                 330                 340                 350                 360
               |                   |                   |                   |                   |
    GCT TTT AGT ACG ACG ACT TAT GTT GGT TTT CAG GCT GTA ATG ACC
    Ala Phe Ser Thr Thr Thr Tyr Val Gly Phe Gln Ala Val Met Thr 370                 380                 390                 400
                       |                   |                   |                   |
    GAG GAA ATG TCA GAA AAA TTT CGC GGT TTG CCT GGA GTA GTT TTC
    Glu Glu Met Ser Glu Lys Phe Arg Gly Leu Pro Gly Val Val Phe 410                 420                 430                 440                 450
               |                   |                   |                   |                   |
    ATT TTG CCT GAT TCA TAT CTA TAT CCA GAA ACA AAG GAG TAC GGA
    Ile Leu Pro Asp Ser Tyr Leu Tyr Pro Glu Thr Lys Glu Tyr Gly
```

FIG. 4(B)

```
            460             470             480             490
             |               |               |               |
GGA GAC AAA TAT GAC AAT GGT GTC ATC ACT CCA AGA CCA CCA CCT
Gly Asp Lys Tyr Asp Asn Gly Val Ile Thr Pro Arg Pro Pro Pro 500             510             520             530             540
     |               |               |               |               |
GTT CAT TAT AGC AGA CCA TCA AGA ACT GAC AGG AAC CGT AAC TAC
Val His Tyr Ser Arg Pro Ser Arg Thr Asp Arg Asn Arg Asn Tyr 550             560             570             580
             |               |               |               |
CGA GGA AAC TAC CAG GAT GGC CCT CCA CAG CAA GGA AAT TAC CAG
Arg Gly Asn Tyr Gln Asp Gly Pro Pro Gln Gln Gly Asn Tyr Gln 590             600             610             620             630
     |               |               |               |               |
AAC AAC CGT CCT CCA CCA GAA GGT GGT TAC CAG AAC AAC CCG CCG
Asn Asn Arg Pro Pro Pro Glu Gly Gly Tyr Gln Asn Asn Pro Pro 640             650             660             670
             |               |               |               |
CAG CAA GGA AAC TAC CAG ACA TAC CGC TCG CAG CAA GAT GGA AGA
Gln Gln Gly Asn Tyr Gln Thr Tyr Arg Ser Gln Gln Asp Gly Arg 680             690             700             710             720
     |               |               |               |               |
GGC TAT GCC CCA CAG CAG AAT TAT GCA CAA GGT GGT CAG GAT GGT
Gly Tyr Ala Pro Gln Gln Asn Tyr Ala Gln Gly Gly Gln Asp Gly 730             740             750             760
             |               |               |               |
AGA GGT TTT GGA AGG AAT GAT TAC ACA GAC CGT TCA GGC TAC AAT
Arg Gly Phe Gly Arg Asn Asp Tyr Thr Asp Arg Ser Gly Tyr Asn 770             780             790             800             810
     |               |               |               |               |
GGA CCC ACT GAT TTT CGA AGT CAA ACT CAG TAC CAA GGG CAT GTA
Gly Pro Thr Asp Phe Arg Ser Gln Thr Gln Tyr Gln Gly His Val 820             830             840             850
             |               |               |               |
AAT CCA GCT GGG CAA GGT CAA GGT TAC AAC AAC CCC CAA GAG CGT
Asn Pro Ala Gly Gln Gly Gln Gly Tyr Asn Asn Pro Gln Glu Arg 860             870             880             890             900
     |               |               |               |               |
ACG AAC TTC TCG CAA GGG CAG GGA GGA GGT TTT AGG CCT GGT GGT
Thr Asn Phe Ser Gln Gly Gln Gly Gly Gly Phe Arg Pro Gly Gly
```

FIG. 4(C)

```
            910             920             930             940
             |               |               |               |
CCT TCA GCA CCT GGG TCT TAT GGC CAA CCA TCA GCA CCT GGA TCT
Pro Ser Ala Pro Gly Ser Tyr Gly Gln Pro Ser Ala Pro Gly Ser 950             960             970             980             990
        |               |               |               |               |
TAT GGT CAA CCT AAT ACA CTT GGT AAC TAT GGG CAG GTA CCT CCA
Tyr Gly Gln Pro Asn Thr Leu Gly Asn Tyr Gly Gln Val Pro Pro 1000            1010            1020            1030
             |               |               |               |
TCA GTG AAT CCT GGT GGT AAC AGA GTT CCT GGT GTG AAT CCT AGT
Ser Val Asn Pro Gly Gly Asn Arg Val Pro Gly Val Asn Pro Ser 1040            1050            1060            1070            1080
        |               |               |               |               |
TAT GGT GGG GAT GGC AGA CAG GGG GCT GGA CCA GCA TAT GGT GGA
Tyr Gly Gly Asp Gly Arg Gln Gly Ala Gly Pro Ala Tyr Gly Gly 1090            1100            1110            1120
             |               |               |               |
GAT AAC TGG CAA AGA GGT TCT GGT CAG TAT CCT AGC CCA GGT GAA
Asp Asn Trp Gln Arg Gly Ser Gly Gln Tyr Pro Ser Pro Gly Glu 1130            1140            1150            1160            1170
        |               |               |               |               |
GGA CAA GGA AAC TGG CAG GGA AGG CAG TAA GAG CTG ACG TGT TCC
Gly Gln Gly Asn Trp Gln Gly Arg Gln 1180            1190            1200            1210
             |               |               |               |
ACT GAA GAC AAG AAT GGC ACT TGA GAT TTA GAA ATC TCC ATC TGT 1220            1230            1240            1250            1260
        |               |               |               |               |
AAA ATA AAC GAC TGT GAT GCA TTA CTC TTT TTT TTT TTC TTG CAT 1270            1280            1290            1300
             |               |               |               |
TTG AAC TCT AAA CTT ATG GGC ATG CGT TAT TAC CAA ACT ACG GAT 1310            1320            1330            1340            1350
        |               |               |               |               |
GCA AAT TCA TTT TAG TTT TTT GGG CCA AAT GTT GGC ATT TTT AAA

AAA
```

FIG. 5(A)

Nucleotide and deduced amino acid sequence for the male flower specific cDNA clone, pMS14.

```
              10                  20                  30                  40
              |                   |                   |                   |
GCA GGG GGG GGG GCA CAG CAA GCC AGC AGA GCA GAA AGC AGC CGC
Ala Gly Gly Gly Ala Gln Gln Ala Ser Arg Ala Glu Ser Ser Arg 50                  60                  70                  80                  90
          |                   |                   |                   |                   |
AGC CCC AGC CCC CAC AAA GAC GAA GGC AAC AAT GGC GCT AGA AGC
Ser Pro Ser Pro His Lys Asp Glu Gly Asn Asn Gly Ala Arg Ser 100                 110                 120                 130
              |                   |                   |                   |
AGC CAC GCC CCC CGC GCA CTC CTC GCG CGT GCC TCG TCC TGC TGG
Ser His Ala Pro Arg Ala Leu Leu Ala Arg Ala Ser Ser Cys Trp 140                 150                 160                 170                 180
      |                   |                   |                   |                   |
TCC TCG GCG GCG GCA CCG GCC CGT CGT CGG TGC TCA GCG CGC CGG
Ser Ser Ala Ala Ala Pro Ala Arg Arg Arg Cys Ser Ala Arg Arg 190                 200                 210                 220
              |                   |                   |                   |
GGC GCA GGA CCG GCG GCA GTG CCT GCC GCA GCT GAA CGC CTC CTG
Gly Ala Gly Pro Ala Ala Val Pro Ala Ala Ala Glu Arg Leu Leu 230                 240                 250                 260                 270
      |                   |                   |                   |                   |
CGG TGC CGC GCG TAC CTG GTG CCG GCG CGC CGG ACC CCA GCG CGG
Arg Cys Arg Ala Tyr Leu Val Pro Ala Arg Arg Thr Pro Ala Arg 280                 290                 300                 310
              |                   |                   |                   |
ACT GCT GCA GCG CTG ACG CGC CGT GTG CAC GAG TGC GCC TGC AGC
Thr Ala Ala Ala Leu Thr Arg Arg Val His Glu Cys Ala Cys Ser 320                 330                 340                 350                 360
      |                   |                   |                   |                   |
ACC ATG GGC ATC ATC AAC AGC CTG CCC GGC CGG TGC CAC CTC GCC
Thr Met Gly Ile Ile Asn Ser Leu Pro Gly Arg Cys His Leu Ala 370                 380                 390                 400
              |                   |                   |                   |
CAA GCC AAC TGC TCC GCT TGA AGC AGG GAC CTG GCA CGC GTG CTG
Gln Ala Asn Cys Ser Ala
```

FIG. 5(B)

```
       410            420            430            440            450
        |              |              |              |              |
CAA TGG ATG GCA GGA GGG GAG AGG AAT AAG AAG TGT TTC CAT TTC
              460            470            480            490
               |              |              |              |
ACA GTG AGA GCA GTC GAG CTC CAA CGT TGT CGT CGT CGT CGT CTT
       500            510            520            530            540
        |              |              |              |              |
CTT CTT TTG ATA TTC AGA CTC TGT CTT GCG GTC TAT ATC ATC AGC
              550            560            570            580
               |              |              |              |
ATA ATA ATA ATA AAA TAA GTA AAA CCA AAA AAA AAA AAA AA
```

FIG. 6(A)

Nucleotide and deduced amino acid sequence for the male flower specific cDNA clone, pMS18.

```
              10              20              30              40
               |               |               |               |
ACA GCA GTA GCA AGA GGG ATA GAG CAA GGC CAC ACA CAC ACA CAC 50              60              70              80              90
               |               |               |               |               |
ACC ACT AGG CTA GGT TAG CCT TTT AAT CGT CGT CGA GAA GCA AGA 100             110             120             130
               |               |               |               |
AGG GCG CTG CAC CAA GCA GGC AAG CAA GAA GAG AGC CGA TCG ACC 140             150             160             170             180
               |               |               |               |               |
GAG AGC TAG CAC GCG ATG GCG AGG TCT TGC CAA GAT GAT GGT GGC
                            Met Ala Arg Ser Cys Gln Asp Asp Gly Gly 190             200             210             220
               |               |               |               |
GCA CGT CTG CTG GCC TTG CGC TGG CGT GTC GAC CGC CGA GGC AGG
Ala Arg Leu Leu Ala Leu Arg Trp Arg Val Asp Arg Arg Gly Arg 230             240             250             260             270
               |               |               |               |               |
AAC ATC AAG ACC ACG ACG ACG GAG AAG AAG GAC GAC GCG GTG GTG
Asn Ile Lys Thr Thr Thr Thr Glu Lys Lys Asp Asp Ala Val Val 280             290             300             310
               |               |               |               |
CAG CCG CAG AGG TTC CGC CCT TCG ACC GCC TCG GCG CGG CGC GTC
Gln Pro Gln Arg Phe Arg Pro Ser Thr Ala Ser Ala Arg Arg Val 320             330             340             350             360
               |               |               |               |               |
CCC GGC GTT CGG CGG CCT CCC CGG CGG CAC GAT TCC TGG CAG CAG
Pro Gly Val Arg Arg Pro Pro Arg Arg His Asp Ser Trp Gln Gln 370             380             390             400
               |               |               |               |
CAT TCC CGG GTT CAG CAT GCC CGG CAG CGG CAG CAG CCT ACC CGG
His Ser Arg Val Gln His Ala Arg Gln Arg Gln Gln Pro Thr Arg
```

FIG. 6(B)

```
     410             420             430             440             450
      |               |               |               |               |
GTT CAG CTT GCC CGG CAG CGG CAC GAT GCC CCT CTT CGG CGG CGG
Val Gln Leu Ala Arg Gln Arg His Asp Ala Pro Leu Arg Arg Arg
                 460             470             480             490
                  |               |               |               |
CTC CCC GGG CTT CAG CGG CTT CGG CGG CAT GCC CGG GTC GCC CAC
Leu Pro Gly Leu Gln Arg Leu Arg Arg His Ala Arg Val Ala His
     500             510             520             530             540
      |               |               |               |               |
CGC CGG CTC CGT CCC CGA GCA CGC CAA CAA GCC CTG AAC GCC AAC
Arg Arg Leu Arg Pro Arg Ala Arg Gln Gln Ala Leu Asn Ala Asn
                 550             560             570             580
                  |               |               |               |
AAG CGT GGT AGT AGA GGT GCT ACT GTT ACT GTA GTA CGT CGT CGT
Lys Arg Gly Ser Arg Gly Ala Thr Val Thr Val Val Arg Arg Arg
     590             600             610             620             630
      |               |               |               |               |
CTT CAT GCA TGC GTG GTT CGT GGT TTC CCT AGC TCC ATA CGA GCA
Leu His Ala Cys Val Val Arg Gly Phe Pro Ser Ser Ile Arg Ala
                 640             650             660             670
                  |               |               |               |
GTA GTT GGG CTT GCA CGT ACC GTA CGT CTA GCT AGC TAT ATA TAT
Val Val Gly Leu Ala Arg Thr Val Arg Leu Ala Ser Tyr Ile Tyr
     680             690             700             710             720
      |               |               |               |               |
GCT TGT GTT CTA CTG CTT TTT AGT TTA ATT ACC TGC CTG CAT TGG
Ala Cys Val Leu Leu Phe Ser Leu Ile Thr Cys Leu His Trp
                 730             740             750             760
                  |               |               |               |
AGA GTT GGA TCT GTT TCA TTT GGT GGT GTT TGC TTT ACT ATT AGG
Arg Val Gly Ser Val Ser Phe Gly Gly Val Cys Phe Thr Ile Arg
     770             780             790             800             810
      |               |               |               |               |
TCA GTA TCT GTT TGT GGA GAC TTG GTG TTT AAT TTA TTT AGC CGT
Ser Val Ser Val Cys Gly Asp Leu Val Phe Asn Leu Phe Ser Arg
                 820             830             840             850
                  |               |               |               |
TTG TGA CTG GTT GTA GCT AGC GGT GGT GCG GTG GTG ATG TTC TTG
Leu
```

FIG. 6(C)

```
    860             870             880             890             900
     |               |               |               |               |
AGG CAT GAA TAA TGC TAC ATG CAT GTG ATG TAT CCA TGT TTT GTG
            910             920             930
             |               |               |
    TGT GGT AAA CCT GTT GTT TGT ATA AGC TGT CCC
```

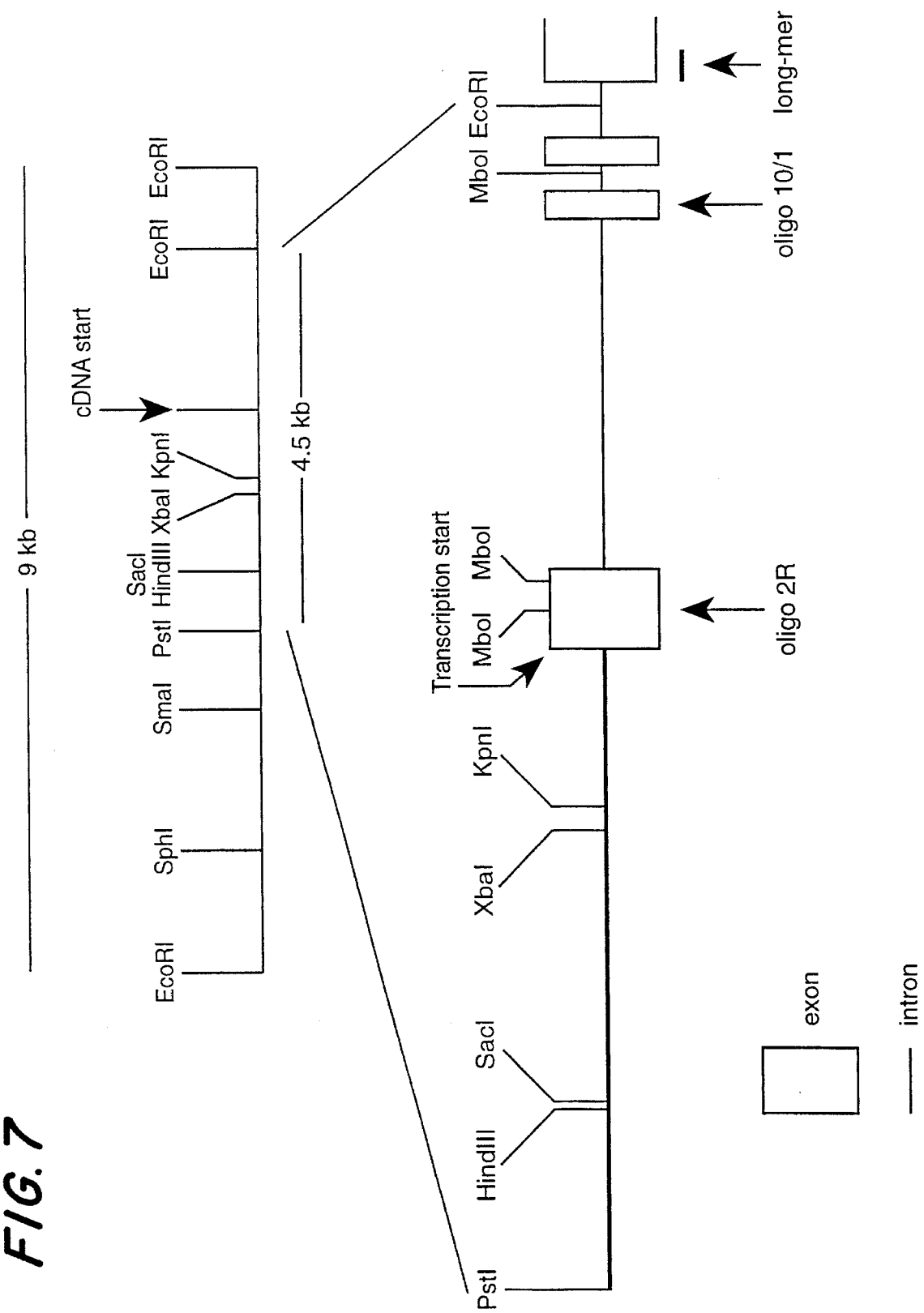

MALE FLOWER SPECIFIC GENE SEQUENCES

This is a continuation of application Ser. No. 08/141,553, filed on Oct. 25, 1993, which was abandoned upon the filing hereof and which is a continuation of application Ser. No. 07/929,494, Aug. 18, 1992, now abandoned, which is a continuation of application Ser. No. 07/931,310, filed Jul. 17, 1991, now abandoned, which is a continuation of application Ser. No. 07/470,604, filed Jan. 26, 1990, now abandoned.

This invention relates to regulatory gene sequences which direct expression of a linked gene specifically to male parts of plants. The sequences to which the invention relates have utility as gene probes for locating male specific sequences in plants generally and is of particular utility in the development of male sterile plants for the production of F1 hybrid plants in situ.

By of general background, F1 hybrid plants are used extensively in most areas of agriculture because of their improved traits of one kind or another, such as increased yield, disease or low temperature resistance. F1 hybrids are produced by a manual process of emasculation of the intended female of the cross, to prevent self pollination, followed by application of pollen taken from the male of the cross to the female pollen receptors of the female of the cross. Maize, a major food crop, is almost exclusively planted as F1 hybrid plants. Maize carries its pollen producing parts as tassels at the terminal of the main stem with the female pollen receptors on quite separate structures in the lower parts of the plant. F1 hybrid production involved interplanting the two partners of the cross and growing to the stage when the tassels first appear. The tassels of the female member of the cross are then mechanically removed so that the female are pollinated by the intended male which is allowed to mature and produce pollen.

The production of such hybrids is clearly labour intensive, which contributes greatly to the increased cost of hybrid seed. It is desirable that a new method be found to simplify the procedure and to reduce cost. One such possible procedure is the utilisation of inherently male sterile plants as the female parent of the cross. Cytoplasmic male sterility (CMS) has been used to advantage in hybrid seed production but the underlying cause of this type of sterility is not well understood and has in the past posed problems of disease such as the Southern corn leaf blight.

An object of the present invention is to provide a new approach to the production of F1 hybrids by manipulation of genes expressed only in the male parts of plants.

According to the present invention there are provided male flower specific cDNA sequences comprising the polynucleotides shown in FIGS. 4(A), 4(B) and 4(C), 5(A) and 5(B), and 6(A), 6(B) and 6(C) herewith, which are specifically expressed in male flower tissue.

The invention also provides the following:

Plasmid pMS10 in an *Escherichia coli* strain R1 host, containing the gene sequence shown in FIGS. 4(A), 4(B) and 4(C) herewith, and deposited with the National Collection of Industrial & Marine Bacteria on 9th Jan. 1989 under the Accession Number NCIB 40090.

Plasmid pMS14 in an *Escherichia coli* strain DH5α host, containing the gene control sequence shown in FIGS. 5(A) and 5(B) herewith, and deposited with the National Collection of Industrial & Marine Bacteria on 9th Jan. 1989 under the Accession Number NCIB 40099.

Plasmid pMS18 in an *Escherichia coli* strain R1 host, containing the gene control sequence shown in FIGS. 6(A), 6(B) and 6(C) herewith, and deposited with the National Collection of Industrial & Marine Bacteria on 9th Jan. 1989 under the Accession Number NCIB 40100.

The isolation and characterisation of these cDNA sequences and the utilisation of these cDNA sequences as molecular probes to identify and isolate the corresponding genomic sequences will now be described.

The clones carrying the genomic sequences and the preparation of a promoter cassette from one of the clones illustrated using an approach and techniques which may be equally applied to any of the the clones. Furthermore the preparation of a promoter fusion to a reporter gene and the transformation of this construct into a test species is described.

Unless stated otherwise, all nucleic acid manipulations are done by standard procedures described in Sambrook, Fritsch and Maniatis, "Molecular Cloning: A Laboratory Manual" Second Edition 1989.

BRIEF DESCRIPTION OF THE DRAWINGS

The drawings which accompany this application show the following:

FIGS. 4(A), 4(B) and 4(C) show the nucleotide and deduced amino acid sequence of MFS cDNA clone pMS10;

FIGS. 5(A) and 5(B) show the nucleotide and deduced amino acid sequence of MFS cDNA clone pMS14;

FIGS. 6(A), 6(B) and 6(C) show the nucleotide and deduced amino acid sequence of MFS cDNA clone pMS18;

FIG. 7 is a restriction map of the 9kb EcoRI fragment from clone 10/CT8-3;

EXAMPLE 1

1. Isolation and Characterisation of Male Flower Specific cDNA from Maize

Figure 1:
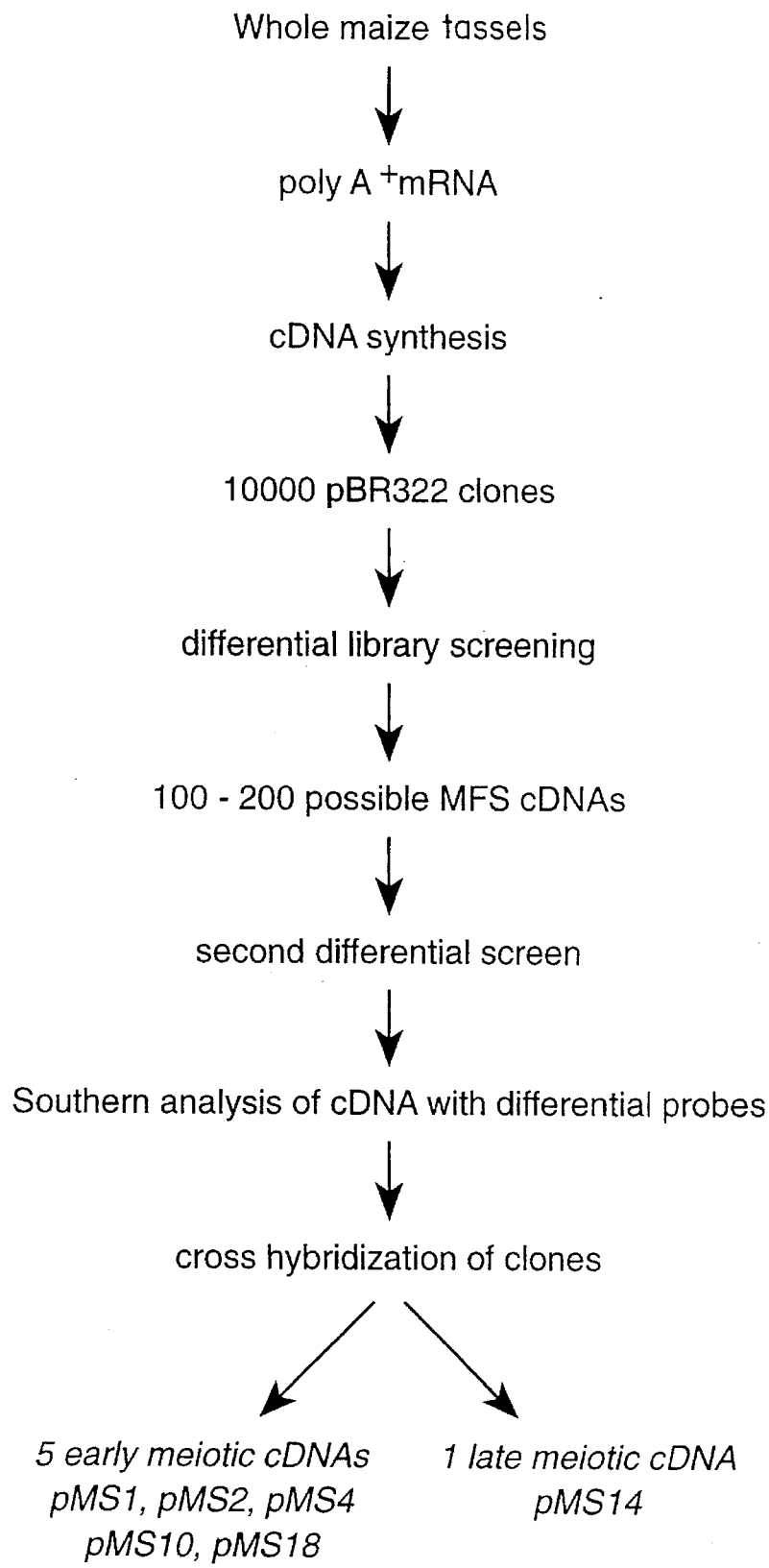
FIG. 1 shows the library screening procedure used for the isolation of maize flower specific clones.

To clone cDNAs to genes which are expressed in the male flowers of maize we constructed two cDNA libraries. In maize, the male flowers are born in the tassel which terminates the main stem. Library 1 was prepared from poly [A] RNA from whole maize tassels bearing early meiotic anthers (most meiocytes in early meiotic prophase) and library 2 from poly [A]+ RNA from whole tassels bearing late meiotic anthers (predominantly diad and early tetrad stages). FIG. 1 reviews the library screening procedure used and this yielded five unique early meiotic MFS cDNAs and one unique late meiotic cDNA. Clone PMS3, a partial cDNA of 120 base pairs, isolated by the differential screening process, was subsequently used as a hybridisation probe to isolate the corresponding pending near full-length clone, PMS18.

Table 1 below summarizes some of the features of each of these cDNA clones. Expression of the mRNAs of the five MFS cDNAs isolated from the early meiotic library is detected in RNA isolated from both early and late meiotic tassel samples. The mRNAs corresponding to these cDNAs are not wholly specific to male flowers and are detected at considerably lower levels in leaves (pMS10 and pMS18) or in leaves, cobs and roots (pMS1, pMS2 and pMS4) Table 1. In contrast pMS14 mRNA is found only in late meiotic RNA and is not detected in leaves, cobs or roots (Table 1).

TABLE 1

| | pMS1 | pMS2 | pMS4 | pMS10 | pMS14 | pMS18 |
|---|---|---|---|---|---|---|
| Library[1] | 1 | 1 | 1 | 1 | 2 | 1 |
| Insert size[2] | 750 | 500 | 720 | 1350 | 620 | 940 |
| mRNA size[3] | 900 | 950 | 850 | 1600 | 900 | 1100 |
| Organ specificity[4] | + | + | + | ++ | +++ | ++ |
| Expression window[5] | E/L | E/L | E/L | E/L | L | E/L |

Table Legend
[1]Isolated from CDNA library 1 (early meiotic) or library 2 (late meiotic).
[2]Approximate size in base pairs.
[3]Approximate size in nucleotides.
[4]+ = in tassels and at much lower levels in leaves, cobs and roots.
++ = expressed in tassels only and at much lower levels in leaves.
+++ = expressed in tassels only.
[5]E/L = MRNA present in RNA from both early and late meiotic tassels.
L = MRNA present only in RNA from late meiotic tassels.

Figure 2:
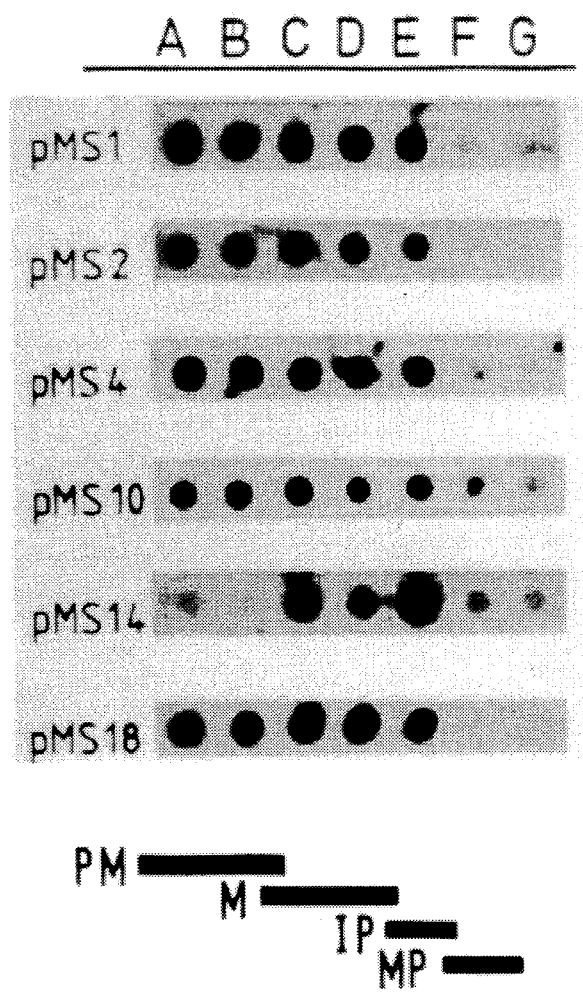
FIG. 2 shows dot blot analysis of total RNA (4 µg per dot) extracted from maize tassels of increasing length.

We have examined expression of the genes corresponding to these cDNAs during tassel development using dot blot hybridisations (FIG. 2). The dot blot analysis was generated by binding total; RNA to nitrocellulose followed by hybridisation to radiolabelled pMS cDNAs. All filters were exposed to film for 48 hours at −70° C. except pMS10 which was exposed for 168 hours. The tassel lengths in each sample were as follows: A≧2 cm; B=2–5 cm; C–5–10 cm; D=10–15 cm; E=15–20 cm; F=20–30 cm; and G=20–30 cm. The solid bars in FIG. 2 show the developmental stage relative to microsporogenesis in each of the samples: PM=premeiosis; M=meiosis; IP=immature pollen; and MP=mature pollen.

The early meiotic mRNAs (pMS1, 2, 4, 10 and 18) accumulate very early in development in tassels less then 2 cm in length. We have not analysed expression in floral meristems prior to this stage. These mRNAs persist through the meiotic anther stages and then decline as pollen grains mature. In contrast the late meiotic mRNA of pMS14 is not detected in tassels less then 5 cm in length, but increases dramatically as the sporogenous cells of the anther enter meiosis (FIG. 2). As with the early meiotic mRNAs, pMS14 mRNA declines abruptly as mature pollen accumulates in the anthers (FIG. 2).

These data show that different temporal controls of gene expression occur during development of male flowers in maize. The controls which programme accumulation of the early meiotic mRNAs are probably very similar but contrast markedly with those regulating appearance and accumulation of the late meiotic mRNA, pMS14. Both the early and late meiotic mRNAs are involved with developmental processes which occur prior to the accumulation of mature pollen grains. They are clearly not involved with the later stages of anther development such as dehiscence nor are they mRNAs which accumulate in mature pollen.

The technique of in situ hybridisation has been used to determine the tissue localisation of MFS mRNAs in male flowers of maize. The techniques used are described in Wright and Greenland (1990; SEB Seminar Series, vol 43 ed by N Harris and D Wilkman. Cambridge University Press, Cambridge; in the Press). The data shown is that for pMS14 mRNA.

Figure 3A:
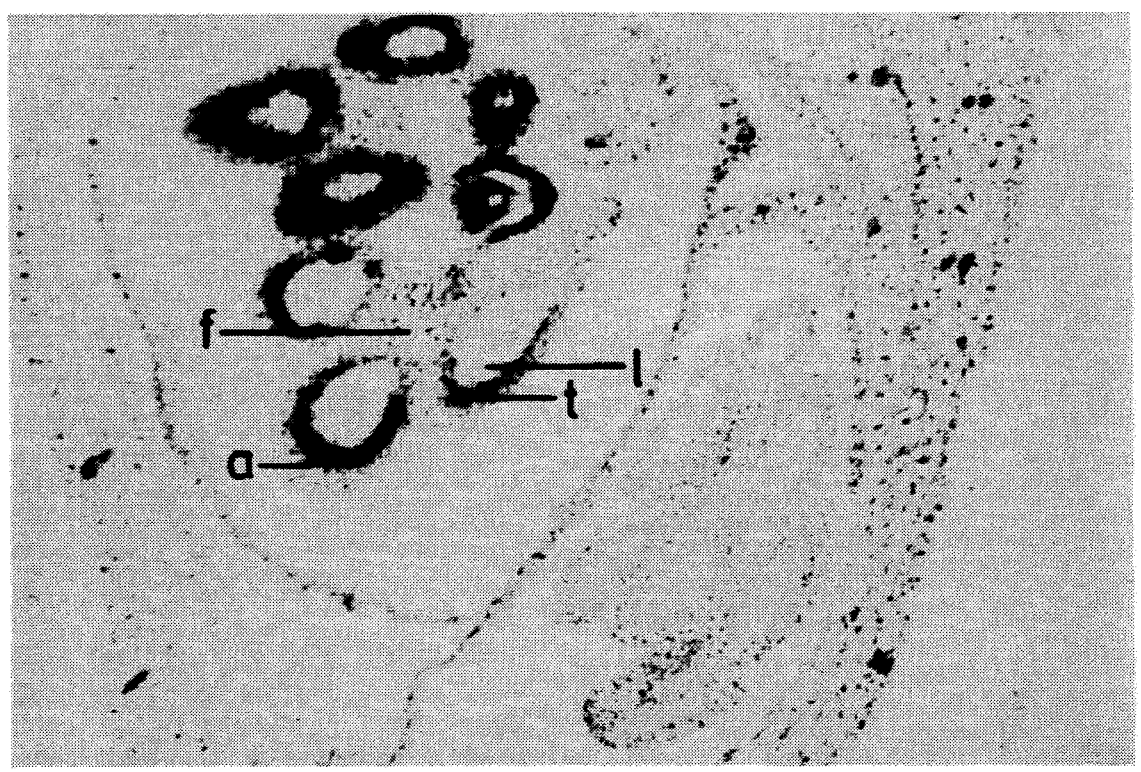
FIGS. 3A, 3B, 3C show in situ hybridisation of maize spikelet sections with pMS14 antisense RNA probes.
Figure 3B:
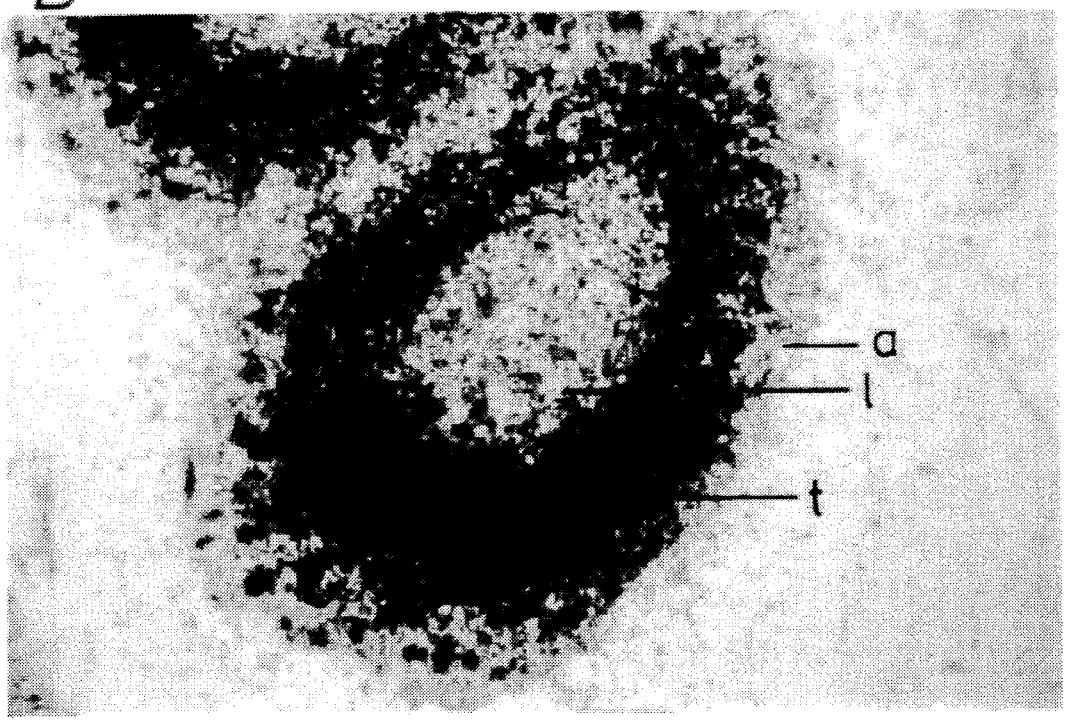
Figure 3C:
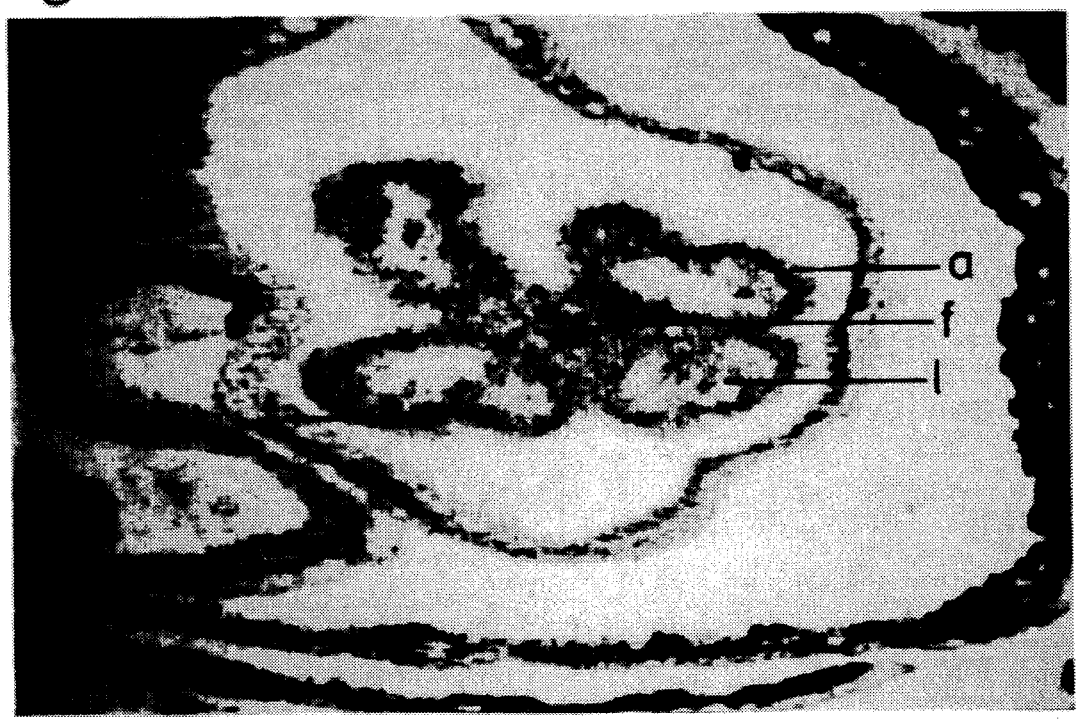

FIGS. 3A, 3B shows in situ hybridisation with pMS14 antisense RNA probes. Sense and antisense probes were prepared by sub cloning a 300 basic pair fragment of pMS14 into the vector, pBS, followed by preparation of radiolabelled T3 and T7 polymerise transcripts utilising methods suggested by the supplier of the vector (STRATAGENE, Trade Mark). These hybridisations show that pMS14 mRNA is located in the tapetal cell layer (referenced "t" in the Figures) surrounding the developing microspores. Hybridisation of the pMS14 antisense probe does not occur to any other cells in the section. Likewise the pMS14 sense probe does not show any specific hybridisation (FIG. 3c). These sections were made from 15–20 cm maize tassels at a stage when the level of pMS14 mRNA is at a maximum (FIG. 2). In these sections and in those from subsequent experiments hybridisation occurs to the tapetum of the anthers (referenced "a" in the Figures) in one floret but not the other. In FIGS. 3A, 3B the tapetal layers which contain pMS14 mRNA surround late meiotic microspores at the tetrad stage whilst the tapetal layers not containing pMS14 mRNA surround sporogenous cells which have not undergone meiosis. It is a feature of maize that the sets of anthers within the individual florets of the spikelet do not develop co-ordinately. Thus in situ hybridisation shows that accumulation of pMS14 mRNA is tissue-specific and confirm data obtained from dot blot analysis (FIG. 2) that expression of PMS14 mRNA is stage specific as it is first detected in tapetum surrounding meiotic cells. Other plant physiological structures evident in FIGS. 3A, B and C are the locules "l" and the filament "f".

EXAMPLE 2

Determination of DNA sequence of pMS10

DNA from cDNA clone, pMS10, for sequence analysis by subcloning into M13mp18 using standard procedures. The nucleotide sequences of the subclones were determined by the dideoxy method using standard procedures. In addition a SEQUENASE (Trade Mark) method was used utilising methods described by the suppliers. Regions of the clones were sequenced by priming with synthetic oligonucleotides synthesised from sequence obtained from previous gel readings. Oligonucleotide concentrations used for priming were identical to those-used with universal primers.

MFS, Clone pMS10 full length cDNA of 1353 base pairs. The complete nucleotide sequence and the predicted amino acid sequence are shown in FIGS. 4(A), 4(B) and 4(C). The sequence contains an open reading frame of 1022 nucleotides encoding a polypeptide of 341 amino acids with a deduced molecular weight of 37371 kd the polypeptide is rich in glycine residues. The open reading frame is flanked by 5' and 3' non-translated regions of 129 and 201 bases respectively.

EXAMPLE 3

Determination of DNA sequence of pMS14

Procedure of determining nucleotide sequence as described in Example 2.

Clone pMS14 is an in complete cDNA of 581 base pairs the complete nucleotide sequence and deduced amino acid sequence are shown in FIGS. 5(A) and 5(B). The sequence contains an open reading frame which extends from nucleotide 1 to 278 encoding a partial polypeptide of 127 amino acids. The polypeptide is particularly rich in alanine and arginine residues. The open reading frame is flanked by 3' non-coding region 203 nucleotides. A consensus processing and polyadenylation signal hexanucleotide, AATAAA occurs at position 548.

EXAMPLE 4

Determination of DNA sequence of pMS18

Procedure for determining nucleotide sequence as described in Example 2.

Clone pMS18 is a near full-length cDNA of 933 bases. The complete nucleotide sequence and deduced amino acid sequence is shown in FIG. 6. pMS18 lacks 28 nucleotides at its 3' terminus. The missing nucleotides are present in clone pMJ3 which overlaps the sequence of pMS18 by a further 91 nucleotides. pMS3 was the original clone isolated by differential screening of cDNA libraries and was subsequently used as a hybridisation probe to isolate pMS18. pMS18 contains an open reading frame extending from nucleotide 151 to 813 and encodes a polypeptide of 221 amino acids with a deduced molecular weight of 25 kilodaltons. The polypeptide is particularly rich in arginine residues. The open reading is flanked by 5' and 3' non-coding regions of 150 and 120 nucleotides respectively.

EXAMPLE 5

Isolation of genomic clones corresponding to pMS10

Genomic DNA clones carrying genes corresponding to the cDNA, pMS10 were isolated from an EMBL 3 phase library of partial MbO1 fragments of maize DNA. The library was screened using radiolabelled "long-mer" probes synthesised in an in vitro labelling system. This system comprised, 50 ng of a synthetic 100 base oligonucleotide (base position 452–551 at pMS10; FIGS. 4(A), 4(B) and 4(C). 500 ng of a synthetic primer oligonucleotide, sequence—TAGTTTCCT-CGGTAG and which will base pair with the 3' end of the long oligonucleotide, one or two radiolabelled oligonucleotides (usually $^{32}$PdCTP and/or $^{32}$P-dGTP) and 5–10 units of the Klenow fragment of DNA polymerase 1. The reactions were performed at 37° C for 30 minutes in a buffer identical to that used for the "random-priming" method of DNA labelling except that the random hexanucleotides were omitted. Five million phase clones immobilised on nylon "HYBAID" (Trade Mark) filters were hybridised at 65° C. with these probes using prehybridisation and hybridisation buffers suggested by the suppliers of the filters (Amersham International). Filters were washed on 3×SSC, 0.1% SDS at 65° C. using these procedures 50–60 EMBL3 phage clones containing either complete or partial regions of a pMS10 gene were obtained. The DNA from three EMBL3 phage clones 10/CT8-1, 10/CT8-3 and 10/CT25-3 which combined complete pMS10 genes was prepared and analysed by restriction enzyme digests. Each of these clones was shown to contain a common 9 Kb EcoRI fragment which extends from the third intron of the pMS10 gene into the 5' non-coding and promoter regions of the gene. A partial restriction map of the 9 Kb EcoRI fragment is shown in FIG. 7.

EXAMPLE 6

Isolation of genomic clones corresponding to pMS14

Figure 8:
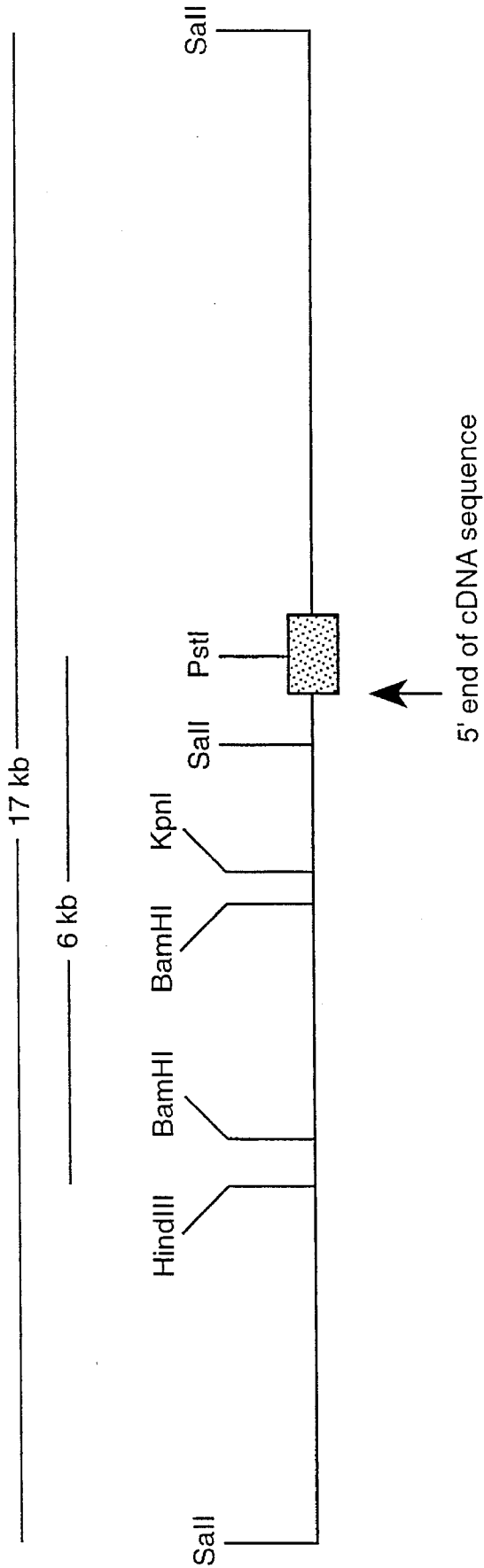
FIG. 8 is a restriction map of the 9kb EcoRI fragment from clone 14/17M.

To isolate genomic DNA clones carrying genes corresponding to the cDNA, pMS14 two approaches were taken. In the first approach the method shown in Example 5 was adopted except the 5 million phage clones were screened with the complete cDNA sequence and the wash stringencies after hybridisation procedure yielded two positive clones 14/CTA and 14/CTD. In the second approach a 12 Kb EcoRI cut fraction of maize geomic DNA, shown by Southern Blotting to carry the pMS14 gene, was ligated into EcoRI cut λ phage EMBL4 DNA to produce a library of cloned 17 Kb DNA fragments. Roughly 200,000 clones were screened as described above, and two positive clones, 14/17m and 14/17R which combined a 17 Kb EcoRI fragment which hybridized to pMS14, were isolated. On further analysis the two positive clones isolated from the partial MboI/EMBL3 library were found to contain an internal 17 Kb fragment. A partial restriction map of this 17 Kb EcoRI fragment, common to all the clones, is shown in FIG. 8.

EXAMPLE 7

Isolation of genomic clones corresponding to pMS18

Figure 9:
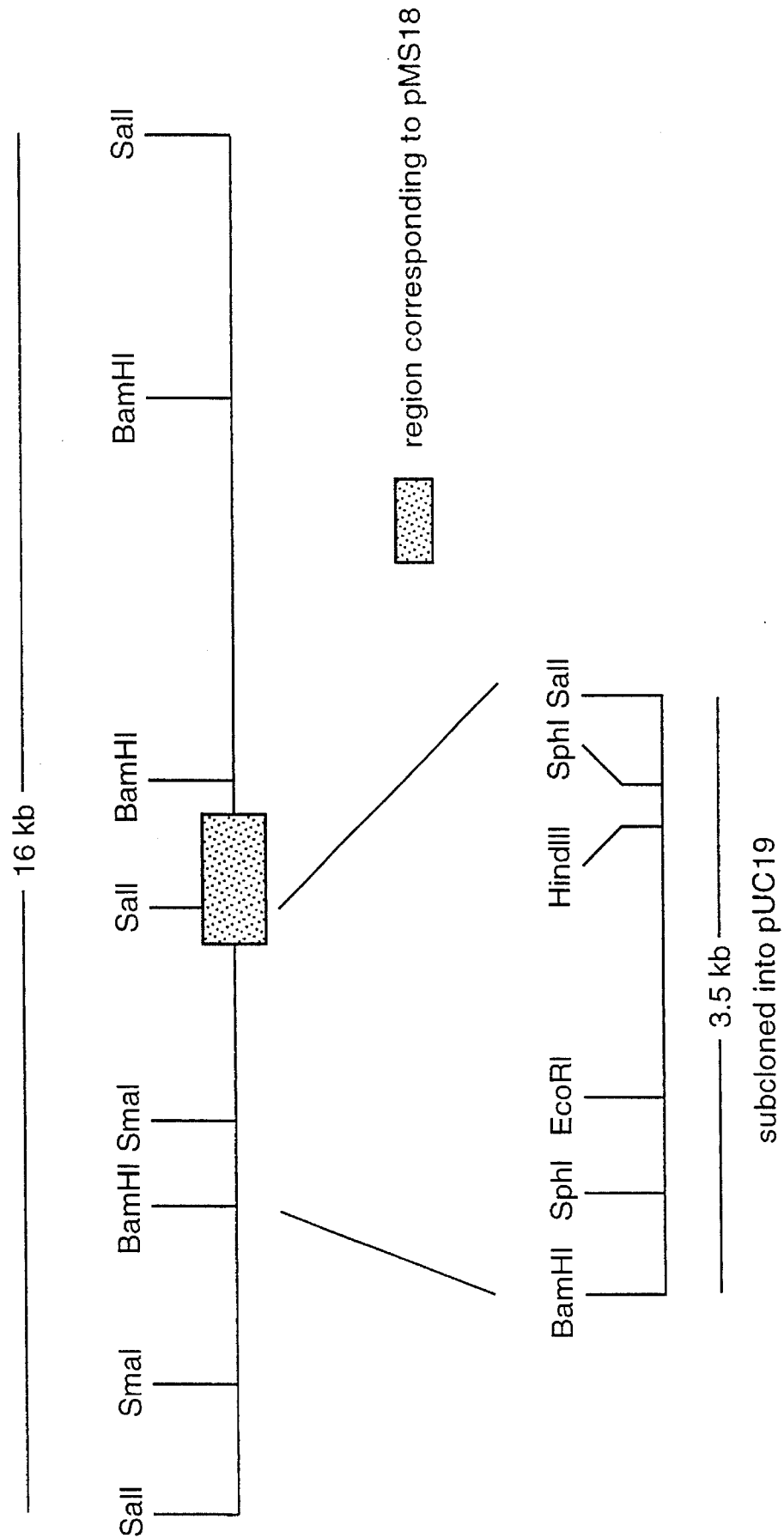
FIG. 9 is a restriction map of the 9kb EcoRI fragment from clone 18/CT3.
Figure 10:
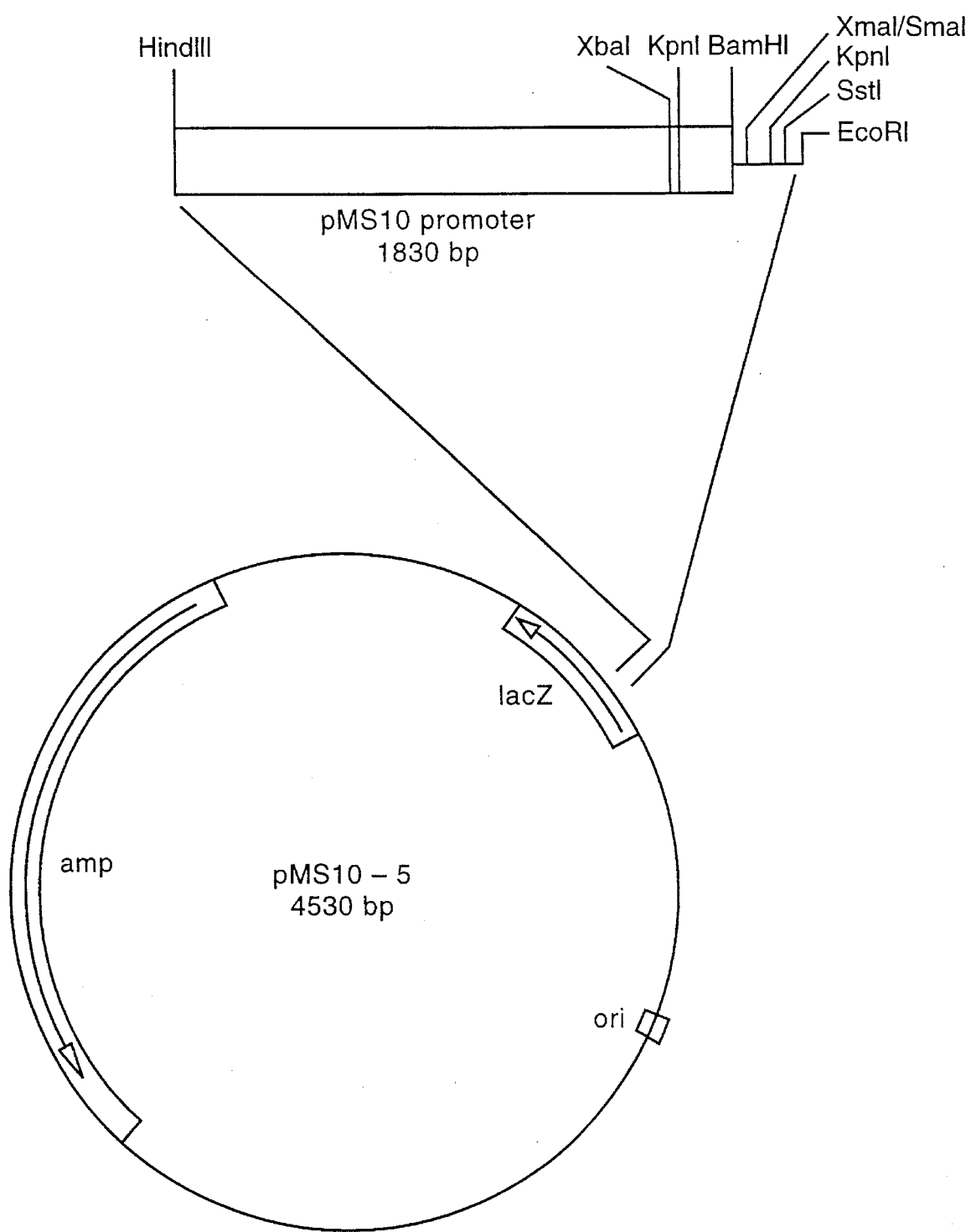
FIG. 10 is a plasmid map of clone pMS10-5.

To isolate genomic DNA clones carrying genes corresponding to the cDNA pMS18, the procedure described in Example 5 was adopted. Five million EmBL3 phage clones were hybridized to a "long-mer" probe derived from the sequence of pMS18, position 133–222 (FIG. 5(A) and 5(B)). The sequence of the 3' complementary oligonucleotide was a 5'-GCCTCGGCGGTCGAC-3'. Two clones, 18/CT3 and 18/CT23, carrying the pMS18 gene were isolated from this screen. Restriction mapping of these clones showed that they both contained a 4.5 Kb BamHI-SalI fragment comprising the 5' region of the coding sequence of pMS18 and approximately 4 Kb of the promoter and upstream region of the gene. A partial restriction map of clone 18/CT3 is shown in FIG. 9.

EXAMPLE 8

Construction of a promoter cassette derived from 10/CT8-3

The following subclones from the λEMBL3 clone 10/CT8-3 were made. The 4.5 Kb PstI-EcoRI fragment was cloned into pUC18 to give pMS10-2. The 2.7 Kb XbaI-EcoRI fragment was cloned into pUC 18 to give pMS10-3. The 1.6 Kb HindIII to XbaI fragment was cloned into pUC18 to give pMS10-4.

The polymerase chain reaction (PCR) was used to amplify a 930 bp fragment from pMS10-3. The primers used for the PCR reaction were as follows. Primer pUC/2 is homologous to pUC sequence flanking the polylinker site. Primer 10/9 is complementary to the sequence of pMS10 from position 106–129 except that it contains an additional thymidine residue between bases 123 and 124. The sequence of these primers is:

pUC/2 5' CGACGTTGTAAAACGACGGCCAGT-3'

10/9 5' AGTCGGATCCCGCCCCGCGCAGCCG-3'

Following amplification in the PCR reaction a DNA fragment is produced in which the flanking XbaI site and the sequence identical to that present in the corresponding region of clone 10/CT8-3 up to the base immediately prior to the translation initiator are faithfully reproduced except that a novel BamHI site is introduced by the introduction of the thymidine residue. This 930 bp fragment was gel purified, and digested with XbaI and BamHI. It was then cloned into pMS10-4 which had been previously digested with XbaI and BamHI to yield clone pMS10-5. In pMS10-5 the sequences required for promoter activity associated with the MS10 gene are reacted and modified such that the promoter can now be fused to any gene via the BamHI site which occurs immediately prior to the translation start point. That these and no other modifications had occurred was confirmed by sequence analysis.

EXAMPLE 9

Figures 11A, 11B:
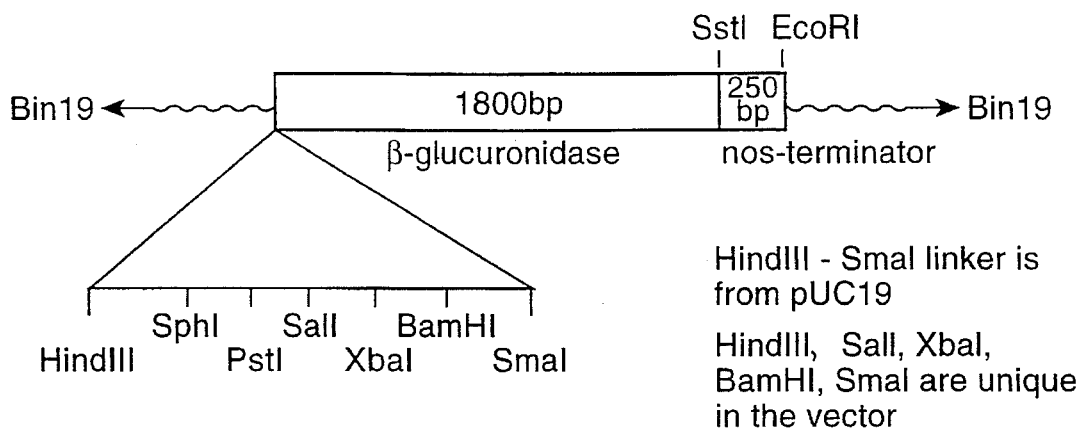
FIG. 11 shows the structure of pTAK1, pTAK2 and pTAK3.
Figure 12:
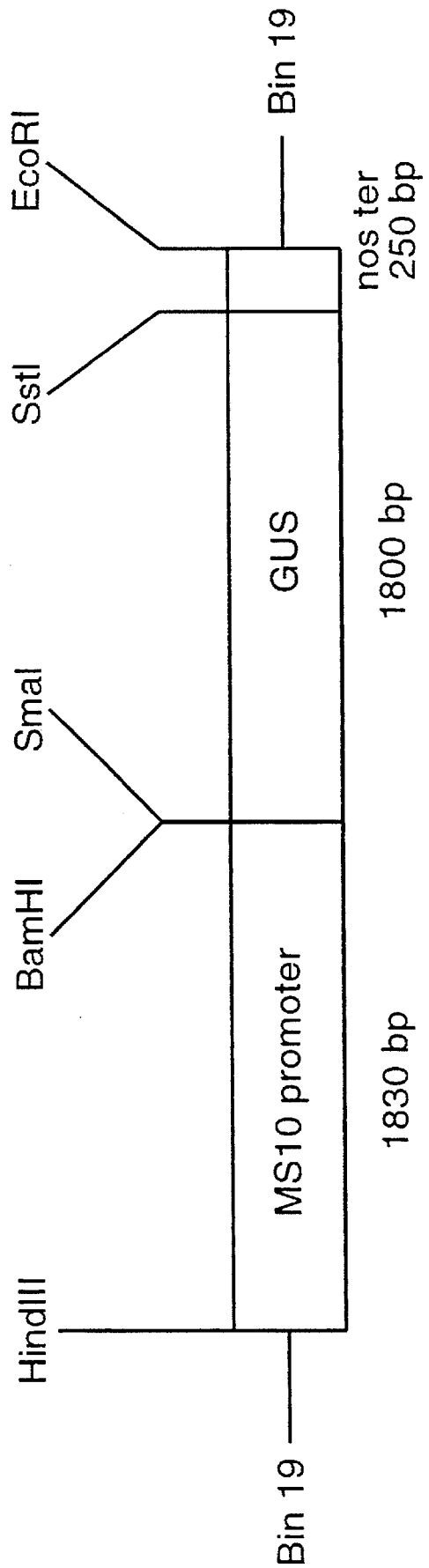
FIG. 12 is a map of clone pMS10-6GUS.

Construction of a promoter fusion between MS10 gene and the glucuronidase reporter gene The 1830 bp HindIII to BamHI fragment from pMS10-5 was ligated into pTAK1, previously cut with HindIII and BamHI. pTAK1 is based on the binary plant transformation vector Bin 19 (Bevan, 1984; Nucleic Acids Research 12, 8711) and carries the glucuronidase (GUS) reporter gene and Nos 3' terminator (FIG. 11). The resulting plasmid was termed pMS10-6GUS and makes a transcriptional gene fusion between the promoter of the MS10 gene and the GUS reporter gene.

EXAMPLE 10

Transformation of tobacco plants with MS10 promoter gene constructs

The recombinant vector pMS10-6GUS as mobilised from *E. Coli* (TG-2) onto *Agrobacterium tumefaciens* (LBA4404) in a triparental mating on L-plates with *E Coli* (HB101) harbouring pRK2013. Transconjugants were selected on minimal medium containing kanamycin (50 g/cm$^3$) and streptomycin (500 µg/cm$^3$).

L-Broth (5 cm$^3$) containing kanamycin at 50 g/cm$^3$ was inoculated with a single Agrobacterium colony. The culture was grown overnight at 30° C. with shaking at 150 rpm. This culture (500 µl) was inoculated into L-Broth containing kanamycin (50 µ g/cm$^3$) and grown as before. Immediately before use the Agrobacteria were pelleted by spinning at 3000 rpm for 5 minutes and suspended in an equal volume of liquid Murashige and Skoog (MS) medium.

Feeder plates were prepared in 9 cm diameter petri dishes as follows. Solid MS medium supplemented with 6-benzyl-aminopurine (6-BAP) (1 mg/l) and 1-naphthaleneacetic acid (NAA) (0.1 mg/l) was overlaid with *Nicotiana tabacum* var Samsun suspension culture (1 cm$^3$). One 9 cm and one 7 cm filter paper discs were placed on the surface.

Whole leaves from tissue culture grown plants were placed in the feeder plates. The plates were sealed with "NESCOFILM" (Trade Mark) and incubated overnight in a plant growth room (26° C. under bright fluorescent light).

Leaves from the feeder plates were placed in Agrobacteria suspension in 12 cm diameter petri dishes and cut into 1–1.5 cm$^2$ sections. After 20 minutes the leaf pieces were returned to the feeder plates which were sealed and replaced in the growth room. After 48 hours incubation in the growth room the plant material was transferred to MS medium supplemented with 6-BAP (1 mg/l), NAA (0.1 mg/l), carbenicillin (500 µg/cm$^3$) and kanamycin (100 µg/cm$^3$), in petri dishes. The petri dishes were sealed and returned to the growth room.

Beginning three weeks after inoculation with Agrobacterium, shoots were removed from the explants and placed on MS medium supplemented with carbenicillin (200 µg/cm$^3$) and kanamycin (100 µg/cm$^3$) for rooting. Transformed plants rooted 1–2 weeks after transfer.

Following rooting, transformed plants were transferred to pots containing soil and grown in the glasshouse. Roughly one month after transfer the plants flowered.

The anthers of the tobacco plants containing the pMS10-6GUS construct were sprayed for GUS activity using standard procedures.

We claim:

1. A plant gene construct comprising a structural gene of interest operably linked to the male flower specific promoter sequence which comprises the polynucleotide sequence of FIG. 4, which said structural gene is specifically expressed in male flower tissue, or a mutant or variant of the promoter sequence which retains said tissue specificity.

2. A plant gene construct as claimed in claim 1, in which the male flower specific promoter is isolated from the plasmid pMS10 having been deposited in an *Escherichia coli* strain R1 host, with the National Collection of Industrial & Marine Bacteria on Jan. 9, 1989 under Accession Number NCIB 40090.

3. A plant gene construct comprising a structural gene of interest operably linked to the male flower specific promoter sequence which comprises the polynucleotide sequence of FIG. 5, which said structural gene is specifically expressed in male flower tissue, or a mutant or variant of the promoter sequence which retains said tissue specificity.

4. A plant gene construct as claimed in claim 3, in which the male flower specific promoter is isolated from the plasmid pMS14 having been deposited in an *Escherichia coli* strain DH5α host, with the National Collection of Industrial & Marine Bacteria on Jan. 9, 1989 under Accession Number NCIB 40099.

5. A plant gene construct comprising a structural gene of interest operably linked to the male flower specific promoter sequence which comprises the polynucleotide sequence of FIG. 6, which said structural gene is specifically expressed in male flower tissue, or a mutant or variant of the promoter sequence which retains said tissue specificity.

6. A plant gene construct as claimed in claim 5, in which the male flower specific promoter is isolated from the plasmid pMS18 having been deposited in an *Escherichia coli* strain R1 host, with the National Collection of Industrial & Marine Bacteria on Jan. 9, 1989 under Accession Number NCIB 40100.

* * * * *